(12) United States Patent
Kang et al.

(10) Patent No.: US 8,382,812 B2
(45) Date of Patent: Feb. 26, 2013

(54) APPARATUS FOR PHOTODYNAMIC THERAPY AND PHOTODETECTION

(75) Inventors: Uk Kang, Ansan-si (KR); Garri. V Papayan, Saint Petersburg (RU)

(73) Assignee: Korea Electro Technology Researc Institute, Gyeongsangnam-Do (KR)

( * ) Notice: Subject to any disclaimer, the term of this patent is extended or adjusted under 35 U.S.C. 154(b) by 938 days.

(21) Appl. No.: 12/473,745

(22) Filed: May 28, 2009

(65) Prior Publication Data

US 2010/0145416 A1 Jun. 10, 2010

(30) Foreign Application Priority Data

Dec. 10, 2008 (KR) ........................ 10-2008-0124970

(51) Int. Cl.
*A61N 5/06* (2006.01)
(52) U.S. Cl. ............................................. 607/90; 606/9
(58) Field of Classification Search .......... 356/300–451; 600/160; 606/9; 607/88–94
See application file for complete search history.

(56) References Cited

U.S. PATENT DOCUMENTS

| | | | |
|---|---|---|---|
| 5,571,108 A | 11/1996 | Amano et al. | |
| 6,208,749 B1 * | 3/2001 | Gutkowicz-Krusin et al. | 382/128 |
| 6,571,118 B1 * | 5/2003 | Utzinger et al. | 600/476 |
| 6,766,184 B2 | 7/2004 | Utzinger et al. | |
| 7,889,348 B2 * | 2/2011 | Tearney et al. | 356/451 |
| 2002/0035330 A1 | 3/2002 | Cline et al. | |
| 2002/0049386 A1 * | 4/2002 | Yang et al. | 600/476 |
| 2003/0139886 A1 * | 7/2003 | Bodzin et al. | 702/28 |
| 2003/0191368 A1 * | 10/2003 | Wang et al. | 600/160 |
| 2005/0213089 A1 * | 9/2005 | Margalith et al. | 356/300 |
| 2007/0087445 A1 * | 4/2007 | Tearney et al. | 436/172 |
| 2007/0114362 A1 * | 5/2007 | Feng et al. | 250/208.1 |
| 2008/0051664 A1 | 2/2008 | Demos et al. | |
| 2009/0244482 A1 * | 10/2009 | Elsner et al. | 351/206 |

* cited by examiner

*Primary Examiner* — Henry M Johnson, III
(74) *Attorney, Agent, or Firm* — Frommer Lawrence & Haug LLP; Ronald R Santucci

(57) ABSTRACT

The present invention provides an apparatus for photodynamic therapy and fluorescence detection, in which a combined light source is provided to illuminate an object body and a multispectral fluorescence-reflectance image is provided to reproduce various and complex spectral images for an object tissue, thus performing effective photodynamic therapy for various diseases both outside and inside of the body.

For this purpose, the present invention provides an apparatus for photodynamic therapy and photodetection, which provides illumination with light of various wavelengths and multispectral images, the apparatus including: an optical imaging system producing an image of an object tissue and transmitting the image to a naked eye or an imaging device; a combined light source including a plurality of coherent and non-coherent light sources and a light guide guiding incident light emitted from the light sources; a multispectral imaging system including at least one image sensor; and a computer system outputting an image of the object tissue to the outside. Thus, the apparatus for photodynamic therapy and photodetection of the present invention can effectively perform the photodynamic therapy and photodetection by means of the combined light source capable of irradiating light having various spectral components to an object tissue and the multispectral imaging system capable of obtaining images from several spectral portions for these various spectral ranges at the same time, thus improving the accuracy of diagnosis and efficiency of the photodynamic therapy.

40 Claims, 8 Drawing Sheets

Lr405:Laser 405 nm
A_NADH:Absorption spectrum_NADH
Hg 340-26:Hg Lamp 340 ±13nm
A_Flavin:Absorption spectrum_Flavin Ex Flavin:Absorption spectrum_Flavin
Ex PpIx:Absorption spectrum_PpIx
Lr 635:Laser 635 nm
455-30:Hg lamp Ex1 455 ±15nm Blue:Em B,B Channel
Green:Em G,G Channel
Red:Em R,R Channel
Edge_700:Wavelength boundary point of dichroic mirror 700 nm
NIR:Em(FR-NIR),FR-NIR Channel E_NADH:Emission NADH, NADH fluorescent signal
E_Flavin:Emission Flavin, Flavin fluorescent signal
Blue:Em B, B Channel
Green:Em G, G Channel
Barrier415:Barrier Filter edge 415 nm Em Flavin:Emission Flavin, Flavin fluorescent signal
Green:Em G, G Channel
Em_PPIX:Emission Pplx, Pplx fluorescent signal
700:Band pass filter 700 nm
Notch_635:Notch Filter 635 nm
Dichroic 640:Wavelength boundary point of dichroic mirror 640nm
Barrier 500:Barrier filter edge 500 nm Ex PpIx:Absorption spectrum_PpIx
Ex Flavin:Absorption spectrum_Flavin
Hg406-15:Hg Lamp 406 ±7nm
Green:Em G, G Channel
Red:Em R, R Channel
Em_PPIXLEmission PpIx,PpIx fluorescent signal
Em Flavin:Emission Flavin, Flavin fluorescent signal
Barrier 500:Barrier Filter edge 500 nm Blue:Em B, B Channel
Green:Em G, G Channel
Red:Em R, R Channel
Em ICG:Absorption spectrum_ICG
ExICG:ICG fluorescent signal
815-30:Em 815 ±15 nm
Dichroic 790:Wavelength boundary point of dichroic mirror 790 nm
Lr780:Laser 780 nm(Ex2)
Hg+HI_VIS:Hg lamp+Halogen lamp_Visible(Ex1) 400~750 nm

APPARATUS FOR PHOTODYNAMIC THERAPY AND PHOTODETECTION

CROSS-REFERENCE TO RELATED APPLICATION

This application claims the benefit of Korean Patent Application No. 10-2008-0124970, filed on Dec. 10, 2008, the entire disclosure of which is hereby incorporated by reference.

BACKGROUND OF THE INVENTION

1. Field of the Invention

The present invention relates to an apparatus for photodynamic therapy and photodetection, and more particularly, to an apparatus for photodynamic therapy and fluorescence detection, in which a combined light source is provided to illuminate an object body and a multispectral fluorescence-reflectance image is provided to reproduce various and complex spectral images for an object tissue, thus performing effective photodynamic therapy for various diseases both outside and inside of the body.

2. Description of Related Art

These days, diagnostic and therapeutic methods using light are widely used in the treatment of various skin diseases such as acne, chloasma, dark spots, maculae, scars, wrinkles, malignant tumors, etc.

Phototherapy devices used for medical purposes typically include a therapeutic, light source and an optical cable using an optical fiber for delivering a light beam generated from the therapeutic light source to a treatment area of a patient.

In this case, as the light source various lamps such as a halogen lamp, a xenon lamp, a metal halide lamp, a mercury lamp, etc. can be used. Various types of optical fiber light source apparatuses based on these lamps have been developed. Also, various types of apparatuses, which can provide diagnostic images for the visible or near-infrared spectral regions using these light sources, have been developed.

U.S. Pat. No. 6,766,184 discloses a method and apparatus for generating multispectral images of tissue. The apparatus includes an illumination source configured to illuminate the tissue, a detector configured to detect radiation from the tissue, and an analysis unit configured to generate a plurality of multispectral images of the tissue. The multispectral images are used as a diagnostic tool for conditions such as cervical cancer detection and diagnosis. However, in this technique, a single color CCD camera is used as the detector, which can receive only multispectral images contained in the visible spectral range by three spectral channels, and a sensor for producing near-infrared images is not included in the apparatus. Moreover, as a non-coherent light source, only a single light source (pulsed xenon flashlight) is used. Radiation from lamps and laser sources is performed by two different light guides without a collimating optics.

Thus, the above-described U.S. Pat. No. 6,766,184 has problems in that it is impossible to obtain multispectral images by four spectral channels (R, G, B, and NIR) located in the visible and near-infrared spectral ranges at the same time, and further it is impossible to control the spectral configuration of the non-coherent light source in white light illumination.

Moreover, in the case where the apparatus is used as an endoscope, there are problems in that when the illumination is performed through the two difference light guides, one of the two light guides should use the passage of the endoscope so as to deliver two light beams, which makes it difficult to perform the operation and provides different illuminations to the field of view. Moreover, since the collimating optics is not employed, non-uniform illumination is given to the field of view in a colposcope.

Meanwhile, U.S. Patent Publication No. 20080051664 discloses an optical imaging method and apparatus for in-vivo and real-time imaging of bladder cancer and determination of tumor margins. This technique is designed for interior examination of a body using an endoscope. As a detector, an on-chip charge amplification CCD camera, a monochrome camera configured to detect near-infrared images, is used. Thus, to receive two images in various spectral ranges simultaneously, other components of a sensor are used. Therefore, there are problems in that it does not provide a color video for monitoring an object tissue in white light illumination and it is impossible to obtain multispectral images in the visible and near-infrared spectral ranges. Moreover, the apparatus is configured to illuminate the object tissue from lamp and laser light sources with the aid of other light guides. Thus, when the apparatus is used as an endoscope, the instrument channel of the endoscope should be used for the light source illumination through two different light guides, and this makes it difficult to perform the endoscope operation and provides non-uniform illumination to the field of view.

U.S. Patent Publication No. 20020035330 discloses a fluorescence endoscopy video system including a multimode light source that produces light for color and fluorescence imaging modes. However, this system does not include a combined light source that can simultaneously produce wavelengths having two or more differences determined by a user and having a wide spectral range and monochromatic light spectra for photodynamic therapy and/or multispectral fluorescence and reflectance light detection. Thus, it is impossible to excite two different kinds of fluorescent materials by optimum wavelength combination. Moreover, the system does not include an optical imaging system for stereoscopic viewing and projection with an additional optical lens on both sensors of a multispectral imaging system, and thus there is no possibility of recording images under white light and fluorescence at the same time. Furthermore, since the system does not include a movable beam splitter having a dichroic mirror, there is no possibility that the dichroic mirror may be moved out of the optical path. Thus, light loss occurs under operational conditions in which only a color image sensor is used. In addition, there is no means for performing the photodynamic therapy.

Meanwhile, U.S. Pat. No. 5,571,108 discloses a binocular stereo microscope including an observation optical system that enables a direct or optical observation of an object through a TV camera. However, since the camera is disposed in one of stereo paths behind a variable power optical system, only a small amount of illumination light detected by an objective lens of the microscope reaches the camera. Thus, the stereo microscope disclosed in U.S. Pat. No. 5,571,108 has a problem in that a significant loss of optical signals emerging from the objective lens occurs.

SUMMARY OF THE INVENTION

The present invention has been made in an effort to solve the above-described problems associated with prior art. Accordingly, the present invention provides an apparatus for photodynamic therapy and photodetection, which includes a combined light source that can irradiate light having various spectral components to an object tissue, an optical imaging system that can provide direct and three-dimensional images of the object tissue that can be seen with naked eye, and a multispectral imaging system that can obtain images from several spectral portions for these various spectral ranges at the same time, thus performing effective photodetection and photodynamic therapy.

In one aspect, the present invention provides an apparatus for photodynamic therapy and photodetection, which provides illumination with light of various wavelengths and multispectral images, the apparatus including: an optical imaging system producing an image of an object tissue and transmitting the image to a naked eye or an imaging device; a combined light source including a plurality of coherent and non-coherent light sources and a light guide guiding incident light emitted from the light sources; a multispectral imaging system including at least one image sensor; and a computer system outputting an image of the object tissue to the outside.

The combined light source may include a first light source, a second light source, and a third light source.

The first light source may be a mercury lamp.

The second light source may be a halogen lamp.

The third light source may be a laser.

The apparatus may further include a first filter for controlling the light emitted from the mercury lamp as the first light source and introduced into the light guide.

The first filter may be located between the mercury lamp and the light guide and disposed on an optical path for the mercury lamp so as not to interfere with optical paths from the light sources other than the mercury lamp.

The first filter may be provided in the form of a filter wheel to include a plurality of optical elements in divided areas on the rotational surface of the filter wheel.

The plurality of optical elements may include at least two selected from the group consisting of a short-pass filter, a band-pass filter, and a polarizer.

The apparatus may further include a first mirror configured to change the path of light emitted from the halogen lamp as the second light source to be introduced into the light guide.

The first mirror may be a dichroic mirror for selectively transmitting light based on a wavelength.

The apparatus may further include a second filter disposed between the halogen lamp and the first mirror to block infrared radiation.

A laser beam generated from the laser as the third light source may be directly introduced into the light guide.

The third light source may include a plurality of lasers, and a second mirror may be located on the paths of a plurality of laser beams generated from the plurality of lasers such that the plurality of laser beams can be introduced into the light guide through the second mirror.

The second mirror may be a dichroic mirror.

The mercury lamp and the laser may be a mercury lamp having a band-pass filter (327 to 353 nm) and a laser (405 nm) as excitation light sources for simultaneously exciting NADH and flavin.

The mercury lamp and the laser may be a mercury lamp having a band-pass filter (440 to 470 nm) and a laser (635 nm) as excitation light sources for simultaneously exciting flavin and porphyrin.

The apparatus may further include a first attenuator located on the optical path of the first light source to control the amount of light from the mercury lamp.

The apparatus may further include a second attenuator disposed at an inlet of the light guide to control the total amount of light introduced into the light guide.

The apparatus may further include a collimating optics disposed at an outlet of the light guide to provide uniform illumination to the field of view.

The apparatus may further include an attached light guide module provided in the collimating optics to provide illumination to a smaller area.

The light guide may be a liquid light guide.

The optical imaging system may be one selected from the group consisting of an endoscope, an operating stereo microscope, and a colposcope.

When the optical imaging system is the endoscope, the multispectral imaging system may be fixed to an eyepiece of the optical imaging system by means of an adaptor.

When the optical imaging system is the operating stereo microscope, the optical imaging system may include an objective lens and a pair of variable power optical systems, and the multispectral imaging system may be located between the objective lens and the variable power optical systems.

The multispectral imaging system may enter the optical path through a movable folding mirror disposed between the objective lens and the variable power optical systems of the optical imaging system.

The multispectral imaging system may include two image sensors.

The two image sensors may be a color image sensor and a monochrome image sensor.

The multispectral imaging system may further include an optical path split means for splitting incident light to have two optical paths for the color image sensor and the monochrome image sensor.

The objective lens of the multispectral imaging system may be located in front of the optical path split means to project an image to the two optical paths of the color image sensor and the monochrome image sensor simultaneously.

The optical path split means may be a movable folding mirror.

The movable folding mirror may be a dichroic mirror.

The objective lens may include an aperture stop to control the amount of light and the depth of field.

The objective lens may include a focusing element for fine focus adjustment on the object tissue.

Fluorescence detection of NADH and flavin may be simultaneously performed by B and G channels of the color image sensor.

A movable detection filter in the form of a filter wheel may be located in front or rear of the objective lens of the multispectral imaging system, and the movable detection filter may include at least two selected from the group consisting of a long-pass filter, a band-pass filter, a notch filter, an analyzer, and a polarizer.

An infrared blocking filter may be located in front of the color image sensor of the multispectral imaging system, and a far-red/near-infrared filter may be located in front of the monochrome image sensor.

The movable detection filter may include a blocking filter (500 nm) and a notch filter (635 nm) such that fluorescence of porphyrin can be detected by the monochrome image sensor through the far-red/near-infrared filter by the dichroic mirror (edge 640 nm) and, at the same time, fluorescence of flavin can be detected by the color image sensor (G channel).

The apparatus may further include an image processing controlling unit for controlling the color image sensor and the monochrome image sensor.

The apparatus may further include a computer system for outputting an image from the multispectral imaging system to the outside.

BRIEF DESCRIPTION OF THE DRAWINGS

The above and other features of the present invention will be described with reference to certain exemplary embodiments thereof illustrated the attached drawings in which.

DETAILED DESCRIPTION OF THE INVENTION

Hereinafter, preferred embodiments of the present invention will be described in detail with reference to the accompanying drawings.

The present invention provides an apparatus for photodynamic therapy and photodetection, which includes a combined light source that can irradiate light having various spectral components to an object tissue, an optical imaging system that provides direct and three-dimensional images of the object tissue that can be seen with naked eye, and a multispectral imaging system that can obtain images from several spectral portions for these various spectral ranges at the same time, thus performing effective photodetection and photodynamic therapy.

Figure 1:
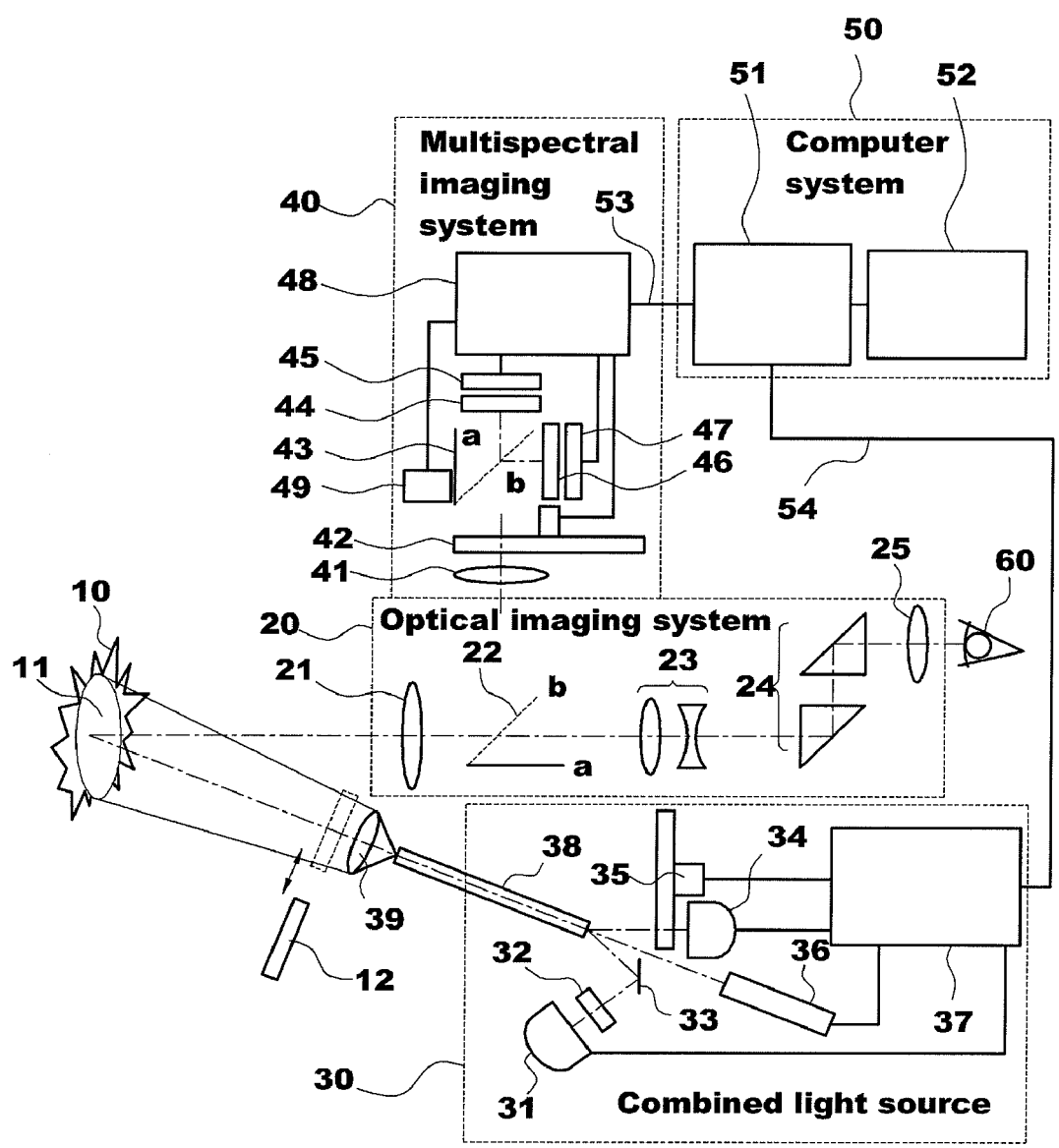
FIG. 1 is a configuration diagram of an apparatus for photodynamic therapy and photodetection in accordance with the present invention.

FIG. 1 is a schematic diagram showing a configuration of an apparatus for photodynamic therapy and photodetection in accordance with the present invention.

As shown in FIG. 1, the apparatus for photodynamic therapy and photodetection in accordance with the present invention generally comprises an optical imaging system 20, a combined light source 30, a multispectral imaging system 40, and a computer system 50, and the apparatus has the functions of illuminating an object tissue of body 10, converting an optical image of the object tissue 10 into an electrical signal, analyzing the optical image, and displaying the optical image on a monitor.

Together with the combined light source 30, the optical imaging system 20 produces images of the object tissue 10 under various illuminations to be seen with naked eye or through a multispectral digital video system. The optical imaging system 20 may be configured as an endoscope, an operating microscope, a colposcope, or any other medical examination apparatus.

In the case where an endoscope is used in conjunction with the configuration of the optical imaging system 20, the multispectral imaging system 40 may be fixed to an eyepiece with the help of an adaptor, and a light guide 38 is connected to an optical channel without a collimating optics 39. Moreover, in the use of a stereo microscope, the multispectral imaging system 40 is inserted into the optical path using a movable mirror 22 disposed between an objective lens 21 and a pair of variable power optical systems 23. These devices play an important role in increasing the amount of light reaching the sensor to obtain a fluorescence image. When the movable mirror 22 is located at 'a', stereoscopic viewing of the object tissue is made, and thus it may be used when the operation is controlled using a tool (e.g., biopsy tongs). When the movable mirror 22 is located at 'b', operations under other conditions may be performed.

That is, since the movable mirror 22 is disposed between the objective lens 21 and the variable power optical systems 23 in the present invention, the optical signals (fluorescence and reflectance light) input to the multispectral imaging system 40 do not pass through the variable power optical systems 23, and thus it is possible to reduce the loss of light.

In the apparatus for photodynamic therapy and photodetection in accordance with the present invention, the combined light source 30 is configured to irradiate light having various spectral components (wavelengths) to the object tissue such that an image is produced by the fluorescence and reflectance light, thus allowing the photodynamic therapy to be performed.

The spectral components of the illumination light are distributed in ultraviolet, visible, and near-infrared spectral ranges, and the illumination light having various spectral components can be simultaneously applied to the object tissue.

Figure 2:
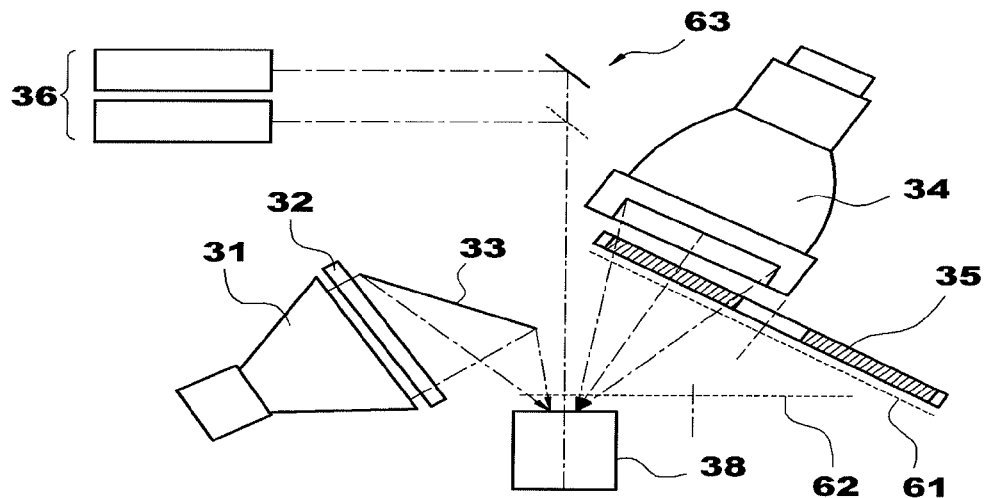
FIG. 2 is a configuration diagram of a combined light source in accordance with the present invention.

The configuration of the combined light source 30 is shown in FIGS. 1 and 2 in detail, and the combined light source 30 includes a halogen lamp 31, an infrared blocking filter 32, a mirror 33, a mercury lamp 34, an illumination filter wheel (Ex1) 35, at least one laser (Ex2) 36, a lighter power supply/control unit 37, a light guide 38, a collimating optics 39, a first attenuator (attenuator 1) 61, and a second attenuator (attenuator 2) 62.

The combined light source 30 in the apparatus for photodynamic therapy and photodetection in accordance with the present invention is configured to include the halogen lamp 31 as a long-wavelength light source and the mercury lamp 34 as a short-wavelength light source. Moreover, the infrared blocking filter 32 reduces the heat load of the object tissue and the light source elements and excludes the radiation spectral components, emitted from the halogen lamp 31, which may be brought into an infrared channel of a detector. An interference filter such as a hot mirror may be employed to conduct such operation.

The mirror 33 changes the direction of light emitted from the halogen lamp 31 to be introduced into the light guide 38, and preferably, the mirror 33 may be configured as a dichroic mirror.

A laser beam generated by the laser 36 is directly introduced into the light guide 38 or through a mirror 63. On the other hand, when the mirror 63 is configured as a dichroic mirror, the laser beams generated by several lasers may be converged by the dichroic mirror. Moreover, the laser 36 includes optical elements for irradiating the laser beam to an end surface of the light guide 38.

The light guide 38 is a liquid light guide having a high numerical aperture, a high transmittance in the ultraviolet (UV), visible (VIS), and near-infrared (NIR) regions, and a high stability under a thermal load of high temperature.

The illumination filter wheel 35 is disposed in an optical path of the mercury lamp 34 and operates in the form of a filter wheel (filter wheel_1). Various optical elements such as short-pass filters, band-pass filters, and a polarizer may be disposed in the respective sectors of the filter wheel that constitutes the illumination filter wheel 35 and configured to control the illumination of the lamps by spectral and polarization states. The illumination filter wheel 35 is disposed between the mercury lamp 34 and the light guide 38 and configured so as not to interfere with the optical paths from the halogen lamp 31 and the laser 36. In this case, the first attenuator 61 for controlling the amount of light generated from the mercury lamp 34 and the second attenuator 62 for controlling the amount of light introduced into the light guide 38 are provided as shown in FIG. 2.

The lighter power supply/control unit 37 supplies electric power to all the light sources and the illumination filter wheel 35 and controls the same.

The collimating optics 39 provided at an outlet of the light guide 38 provides uniform illumination to the field of view (i.e., illuminated area 11 shown in FIG. 1). In this case, an attached light guide module (including a light guide and a collimating optics, not shown) may be installed to provide illumination to an area smaller than the field of view (e.g. conduction of photodynamic therapy for local area) such that the laser beam is irradiated therethrough.

Since the emission spectral range of the combined light source 30 in accordance with the present invention covers a wide spectral range from 300 to 850 nm, the spectral components of the light source can be selected by the requirements of actual application, and the spectral components are determined by supplying electric power to the respective light sources provided in the combined light source 30 and inserting a predetermined filter into the optical path of the mercury lamp 34. Meanwhile, a polarizer 12 may be disposed between the light guide 38 and the object tissue 10 to perform observation by polarization.

Next, examples of the use of the combined light source in the apparatus for photodynamic therapy and photodetection in accordance with the present invention will be described with reference to the following Examples.

Example 1-1

Figure 3:
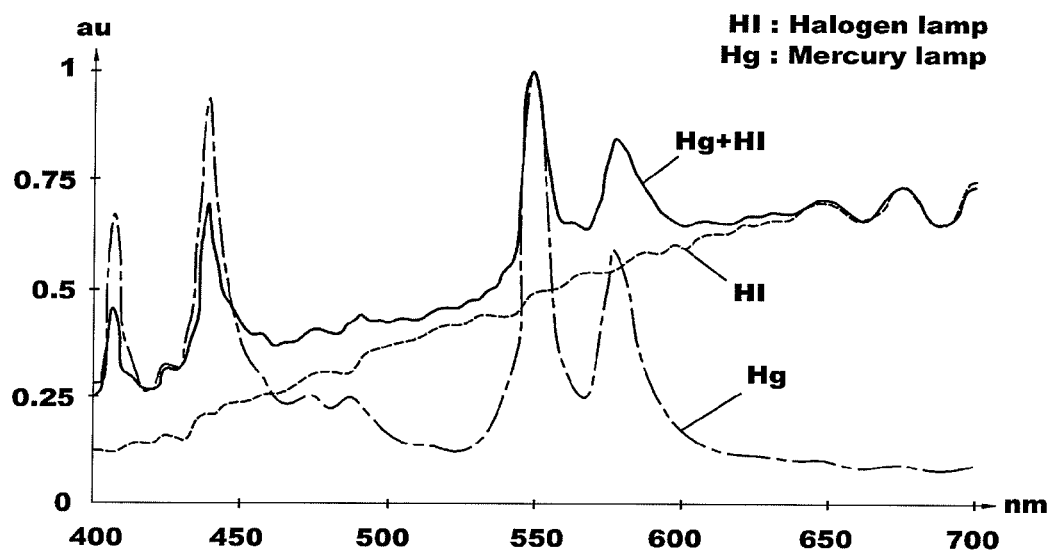
FIG. 3 shows spectral curves over the visible range normalized in the combined light source in accordance with the present invention.

The combined light source 30 of the present invention employs the halogen lamp 31 and the mercury lamp 34 to irradiate white light to the object tissue and observe the reflectance light and defines a wideband filter having a spectral range of 400 to 700 (or 750) nm as the illumination filter wheel 35. The spectral components of the light irradiated to the object tissue can be flexibly changed by mixing the lights emitted from the mercury lamp 34 in various ratios using the first attenuator and the halogen lamp 31. In this case, the correlated color temperature varies in a range of 3,000 to 6,000 K. Spectral curves obtained from this are shown in FIG. 3. As shown in FIG. 3, when the amounts of lights from two lamps are properly complemented by each other, the spectrum is shown as a gentle and continuous curve.

The halogen lamp 31 is widely used as a colposcope light source, and a metal halide and an LED lamp may be used as the light source. Meanwhile, the reason that the combined light source 30 uses the halogen and mercury lamps 31 and 34 in common is to set the intrinsic color temperature of each light source in a proper position. It is possible to change the spectral components of the illumination light to fit the characteristics of the object tissues and the desired operation in the reflectance light by changing the correlation between the amounts of lights emitted from the lamps. Especially, the spectral components of the illumination light are changed to fit the visual perception affected by the various spectral characteristics or to fit the characteristics for television record. Thus, the combined light source 30 in accordance with the present invention allows multispectral analysis in the reflectance light to be optimally performed.

Example 1-2

Excitation of Intrinsic Fluorescence of NADH and Flavin

Figure 4:
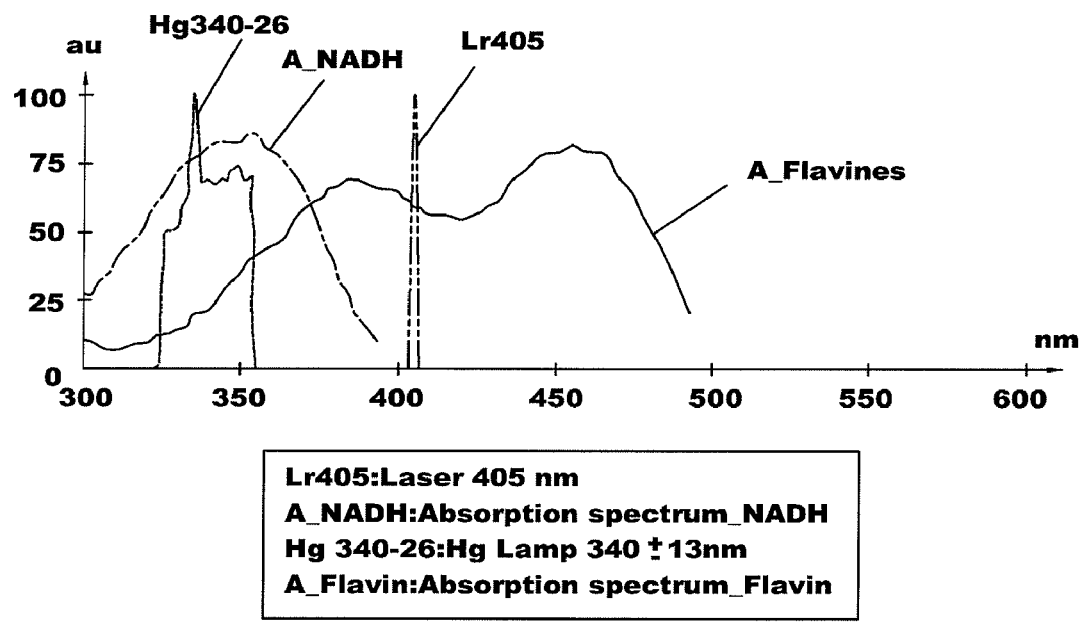
FIG. 4 shows absorption spectral curves of NADH and flavin as fluorescent materials in the combined light source and excitation spectral curves of a mercury lamp having a band-pass filter (340±13 nm) and a laser (405 nm) in accordance with the present invention.

In order to optimally excite these fluorescent materials, one of the excitation lights should be located in the ultraviolet region, and the other should be located at the short-wavelength side of the visible spectral region. The mercury lamp 34 with a band-pass filter (Ex1: 340±13 nm) in the illumination filter wheel 35 and the laser 36 (Ex2: 405 nm) satisfy the above conditions as the excitation light sources. The absorption wavelength bands of the two fluorescent materials are significantly different from each other, and the excitation wavelengths of the excitation light sources fall within these absorption wavelength spectral ranges, respectively (FIG. 4). In this case, the fluorescence emission spectra of the two fluorescent materials are different from each other (FIG. 7), and the fluorescence of the two fluorescent materials can be recorded by a single color detector (refer to Example 2-1 to be described below).

Example 1-3

Excitation of Intrinsic Fluorescence of Flavin and PpIX

Since the light absorption wavelength ranges of the above fluorescent materials overlap in the vicinity of 400 nm, it is possible to excite the fluorescent materials at the same wavelength. However, in this case, the penetration depth of the excitation light is not so large. If the fluorescent materials are excited at a long-wavelength side of the light absorption spectrum of protoporphyrin IX (PpIX), the penetration depth of the excitation light is increased, which is very important in finding a tumor located in a deep part of the tissue.

Figure 5:
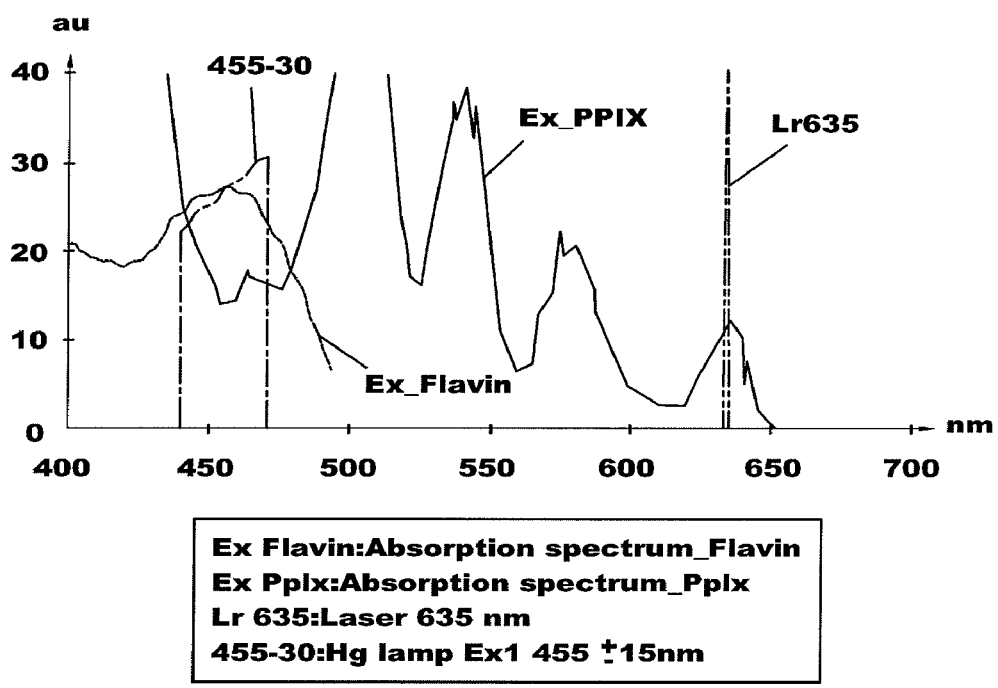
FIG. 5 shows absorption spectral curves of flavin and PpIX in the combined light source and spectral curves of a mercury lamp having a band-pass filter (455±15 nm) and a laser (635 nm) in accordance with the present invention.

FIG. 5 shows absorption spectra of the above-mentioned fluorescent materials and spectra of the two excitation light sources. In connection with the excitation conditions for flavin and PpIX fluorescence detection, the excitation light sources used in the experiment were the mercury lamp 34 with a band-pass filter (Ex1: 455±15 nm) and the laser 36 (Ex2: 635 nm). Since the outputs of the two light sources can be independently controlled, it is possible to properly control the intensities of signals generated from the two fluorescent materials.

Meanwhile, the apparatus for photodynamic therapy and photodetection in accordance with the present invention includes the multispectral imaging system 40 to produce digital video images in several spectral regions of the visible and infrared spectral ranges simultaneously. The multispectral imaging system 40 includes an objective lens 41, a movable detection filter (Em1) 42, a movable optical path split means 43, an infrared blocking filter 44, a color image sensor 45, a far-red/near-infrared (FR/NIR) filter (Em2) 46, a monochrome image sensor 47, an image processing controlling unit 48, and a driving unit 49.

The multispectral imaging system 40 includes a first optical path and a second optical path such that the incident light directed to the detector by the movable optical path split means 43 like a dichroic mirror is split into two beams. The movable optical path split means 43 may be located at one of two discontinuous positions such as 'a' or 'b' by the switching of the driving unit 49.

The objective lens 41 is located in front of the movable optical path split means 43 to project an image to the two optical paths of the color image sensor 45 and the monochrome image sensor 47 simultaneously. Moreover, the objective lens 41 may include an aperture stop to control the amount of light and the depth of field and a focusing element for fine focus adjustment on the object tissue.

A video system of the multispectral imaging system 40 includes two chips with the same electrical and geometrical parameters (color image sensor 45 and monochrome image sensor 47). The two chips may be formed using CCD, EMCCD, or CMOS technology and may operate either in progressive or interlaced scan mode.

Figure 6:
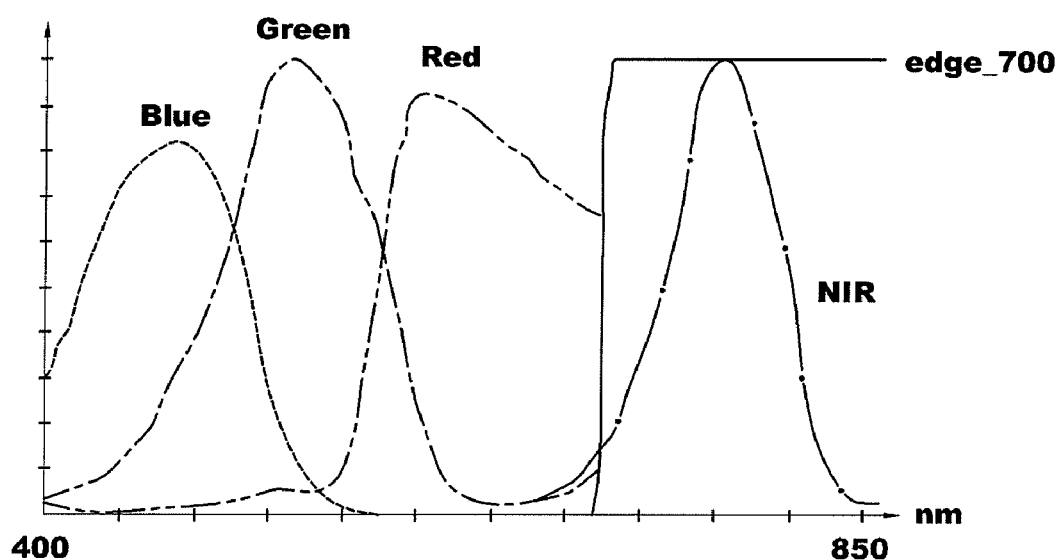
FIG. 6 shows spectral curves of respective channel of a multispectral imaging system in accordance with the present invention.

An optical filter mask having color codes based on RGB model is placed on a photosensitive surface of the color image sensor 45. When another color model, i.e., CMYG, is applied, the computer system 50 converts the CMYG color model into a RGB color code. Thus, three color channels EmR, EmG, and EmB are formed in the first optical path between the two optical paths, and the spectral characteristics of the color channels are determined by the common effect of the RGB mask filters, the movable detection filter (Em1) 42, and the infrared blocking filter 44 (which may be eliminated in a concrete system). The spectral sensitivity of a fourth channel [Em(FR/NIR)] is determined by the FR/NIR filter (Em2) 46, the movable detection filter (Em1) 42, and the dichroic mirrors as the movable optical path split means 43 placed in front of the monochrome image sensor 47 and selecting spectrum. In most cases, the edge of the dichroic mirror is located at the boundary of the visible and near-infrared regions at about 700 nm wavelength, and it may be moved to the long-wavelength or short-wavelength side. As such, the multispectral imaging system 40 can obtain an image from the fourth spectral region simultaneously, which is shown in FIG. 6. When the spectral channels EmR and Em(FR/NIR) cross each other, corresponding optical signals are input to the two channels simultaneously. Each electrical signal value of the two channels depends on a difference in sensitivity of the respective sensors in the two channels as well as the optical signal value. To reduce this cross talk, it is necessary to select elements having appropriate spectral characteristics from the dichroic mirror 43, the infrared blocking filter 44, and the FR/NIR filter (Em2) 46.

The movable detection filter (Em1) 42 is configured in the form of the filter wheel (filter wheel_2) in the multispectral imaging system 40, and various types of barrier filters (long-pass, notch), an analyzer, and a polarizer may be disposed in the respective sectors separated from the shape. The movable detection filter (Em1) 42 may be located in front or rear of the objective lens 41. Since the movable detection filter (Em1) 42 is an element selected for all the optical channels of the two optical paths and is located far way from the surfaces of the detection sensors, the switching operation of the filters is not technically difficult. A change in characteristics of the movable detection filter (Em1) 42 and the illumination filter wheel (Ex1) 35 efficiently changes the operational conditions of the entire apparatus. The operational functions of the movable detection filter (Em1) 42 are as follows:

(a) In the fluorescence diagnosis and photodynamic therapy, it blocks the excitation light and ultraviolet rays (actinic rays) using a notch filter during operation of the laser with the long-pass filter or band-pass filter for the mercury lamp;

(b) It blocks polarized light components using an analyzer in reflected polarization; and (c) It splits the reflectance light into its spectral components, which is necessary for brightness improvement of an image obtained from white light, under reflected color light conditions (e.g., green filter).

The image processing controlling unit 48 controls the monochrome and color image sensors 47 and 45, the driving unit 49, and the filter wheel (filter wheel_2), and converts analog video signals generated by the two sensors into a single digital signal. This digital signal is input to a processor 51 in the computer system 50 through a bidirectional high speed serial bus 53. Besides, a control signal is input and output through the channel. The bidirectional high speed serial bus 53 may operate via firewire, USB, Wi-Fi, etc.

The computer system 50 includes the processor 51 and software related to a monitor 52, which are required to collect, store, process, and analyze video data input from the multispectral imaging system 40, and display a video image through the monitor 52. The analysis includes the function of automatically detecting abnormal tissues based on multispectral information. In addition, the computer system 50 is configured to receive video signals and control all modules of the apparatus through the bidirectional high and low speed serial buses 53 and 54.

As an example of the present invention having the above-described configuration, a digital multispectral video colposcope for photodiagnosis and photodynamic therapy may be used in various modes of operation such as a stereo mode (with a stereo microscope), a reflectance mode, a polarized reflectance mode, a fluorescence detection mode, a photodynamic therapy-fluorescence detection mode, and a fluorescence-reflectance detection mode.

Thus, with the use of the colposcope in accordance with an example of the present invention, various methods for diagnosis and treatment can be realized using the various modes of operation. Some modes have been widely known in the art and applied in other apparatuses.

However, unlike other apparatuses in which only some of the modes can be performed under limited conditions, the colposcope in accordance with an example of the present invention is configured to illuminate an object tissue using several light sources with various wavelengths and, at the same time, detect emission light having several spectral channels so as to satisfy the conditions of the specified modes of operation.

Next, specification requirements and methods needed to realize the specified modes will be described in detail.

1. Stereoscopic Viewing

The stereoscopic viewing in the colposcope is an existing method for visual observation and is used as a control means for diagnosis purpose and various operations. Information that is important in tissue diagnosis is included in epithelial color, and the stereoscopic viewing is possible in the colposcope when the tissue is processed to be expanded using a specific drug such as a solution of acetic acid, Lugol's iodine solution (Schiller's test), etc., or a dye solution such as hematoxylin, methylene violet, etc.

Three-dimensional position control of the colposcope is allowed through the stereoscopic viewing, and the stereoscopic viewing is important to accurately act on the object tissue (e.g., tissue biopsy).

The stereoscopic viewing is possible when a stereo microscope is used as the optical imaging system 20, and is visually performed through a binocular microscope. In this case, the movable mirror 22 is located at 'a'. Moreover, two lamps (halogen and mercury lamps) are used in the combined light source 30. In connection with the illumination filter wheel (Ex1) 35, the spectral components of the total radiation of 400 to 700 nm depend on the correlation between the amounts of lights emitted from the lamps, which can be controlled by adjusting the amount of light emitted from the mercury lamp to a range of 0 to 100% using the first attenuator 1.

For the stereoscopic viewing, the spectral components of the illumination on the object tissue were optimized for visual perception approximate to daylight by adjusting the correlation between the amounts of light emitted from the mercury and halogen lamps, and a color was selected to fit the characteristics of the visual perception of an operator. Thus, a careful selection of illumination reduces eye fatigue during operation and allows the operator to view a minute change in color of the body tissue.

2. White Light Reflectance

The white light reflectance is similar to the stereoscopic viewing, but the difference is that the object tissue is displayed on a monitor in natural color without stereoscopic effect. Thus, the white light reflectance can be observed through any optical imaging system.

In this case, the movable mirror 22 is located at 'b', and the light source is configured under the same conditions as the stereoscopic viewing. Therefore, in the white light reflectance mode, the optimal spectral components of the illumination have a significant difference from the spectral components in the visual perception, and it is possible to adjust the luminescence spectra to fit the characteristics of the color sensor by changing the spectral components of the light source.

3. Polarized Reflectance

In the polarized reflectance, the components of light reflected by the mirror are blocked by a crossed polarizer, and an image is obtained in diffuse reflectance light.

Thus, there is a difference between the polarized reflectance and the white light reflectance. The polarizer 12 was disposed between the optical fiber and the object tissue and a crossed analyzer was used in the movable detection filter 42 together with the polarizer 12. The halogen lamp, the mercury lamp, the laser, or a combination thereof was used as the light source. The spectral characteristics of the illumination depend on the selected emission light source, the illumination filter wheel (Ex1) 35, and the movable detection filter (Em1) 42.

The most significant characteristic of the polarized reflectance is that it is possible to record images in the visible and near-infrared spectral ranges simultaneously. The simultaneous recording of images in the visible and near-infrared spectral ranges during the polarized reflectance is possible by the use of the multispectral imaging system, which increases the possibility of diagnosis by polarization, compared to the color camera (visible rays) disclosed in U.S. Pat. No. 6,766, 184 and the black and white camera (near-infrared rays) disclosed in U.S. Patent Publication No. 2008051664. As an example of this, it is possible to measure oxygen saturation in each region of the body tissue under examination in the vicinity of the first range of 650 to 700 nm and the second range of 800 nm during the recording of two images (Detection of tissue oxygenation in RED/NIR region).

4. Fluorescence Detection

The fluorescence detection was configured to perform diagnosis by fluorescence images obtained from at least one wavelength. Thus, the fluorescence can be realized by irradiating an excitation light having one or two wavelengths to the body tissue (mercury lamp Ex1 or laser Ex2). Moreover, it is possible to record emission in one or two optical channels (color image sensor Em1 or monochrome image sensor Em2).

Therefore, it is possible to observe and measure the components of several fluorescent materials under optimal excitation conditions for each fluorescent material in real time by performing the fluorescence excitation by the emission of light with various wavelengths and the fluorescence detection in several spectral channels simultaneously.

Example 2-1

Autofluorescence Detection of NADH and Flavin

Figure 7:
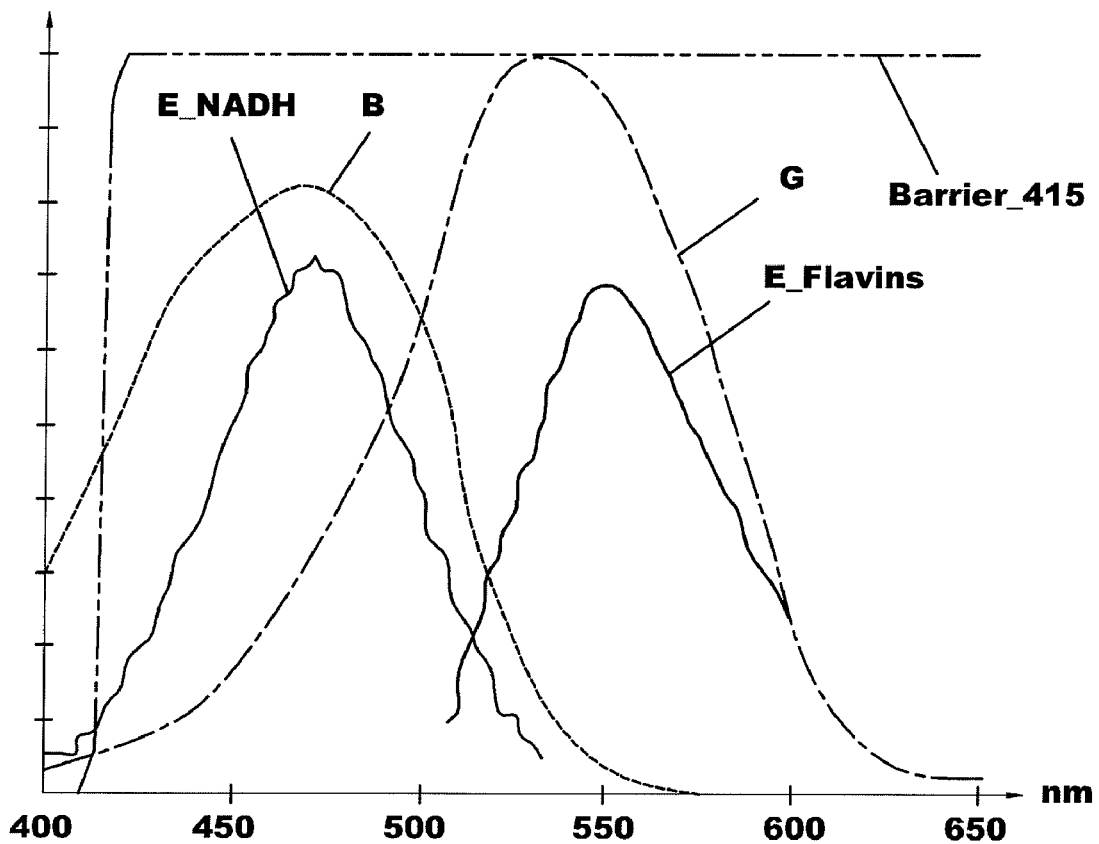
FIG. 7 shows fluorescence emission spectral curves of NADH and flavin and spectral sensitivity curves of B and G channels in the multispectral imaging system in accordance with the present invention.

It is known that the fluorescence characteristics of NADH and flavin as respiratory pigments vary during malignization of the body tissue. According to the apparatus for photodynamic therapy and photodetection in accordance with the present invention, NADH and flavin fluorescence can be recorded simultaneously under optimal excitation conditions. In this case, the excitation conditions of NADH and flavin are the same as those (Ex1: 340 nm, Ex2: 405 nm) proposed in Example 1-2; however, as shown in FIG. 7, the fluorescence can be detected by B and G channels of the color image sensor. That is, as shown in FIG. 7, since the spectral curves of the B and G channels are similar to the fluorescence emission spectra of the fluorescent materials, the fluorescence of NADH can be recorded in the B channel, and the fluorescence of flavin can be recorded in the G channel (B channel: 470 nm center, G channel: 550 nm center). At this time, the barrier filter (415 nm) was used as the movable detection filter to reduce the excitation light reflected from the object tissue. The simultaneous recording of the fluorescence emitted from NADH and flavin can prevent blurred images caused by the movement of the object during exposure and accelerate the measurement process, compared to the sequential recording.

Example 2-2

Autofluorescence Detection of Porphyrin and Non-Porphyrin

Endogenous porphyrin plays an important role in the biological process of the body tissue, and its concentration may vary significantly according to a change in the functional state and during the pathological process. The disturbance of porphyrin metabolism is induced by administration of aminolevulinic acid (ALA). The ALA participates in the process of heme synthesis in the form of porphyrin, and thus the concentration of protoporphyrin IX (PpIX) is repeatedly increased. As a result, it is possible to easily record the fluorescence emitted therefrom. The fluorescence diagnosis by the use of ALA is a well-known method for revealing a series of diseases including malignant tumors in various areas. The absorption wavelength of porphyrin is in the vicinity of 400 nm. When light at this wavelength is irradiated to the body tissue, intrinsic fluorescence (non-porphyrin autofluorescence) is generated together with the porphyrin, which is generated from the fluorescent materials located adjacent to the light absorption wavelengths of the porphyrin, especially from flavins. Since the weak intrinsic fluorescence (autofluorescence) of endogenous porphyrin may not be seen on a bright background of the intrinsic fluorescence of the non-porphyrins, it limits the possibility of observing disorder in the initial step of the pathological process and requires the necessity of increasing the amount of porphyrins that generate fluorescence (ALA-induced protoporphyrin IX fluorescence). In the case where the ALA is administered to the body, it takes a considerable time to confirm the diagnosis of disease, which causes severe limitations on the screening operation for the diagnosis of diseases such as cancer.

Thus, the following problems should be considered to perform the diagnosis without the administration of ALA:

(a) Fluorescence excitation of porphyrin in the spectral region where light is not absorbed by flavin;

(b) Porphyrin fluorescence detection in a position where the fluorescence spectra of flavin and those of porphyrin minimally overlap each other;

(c) Possibility of independently changing the sensitivity of the detector in the multispectral imaging system to allow the signals from the fluorescent materials to be substantially equal to each other; and (d) Possibility of changing the intensity of the fluorescence excitation light of porphyrin and non-porphyrin, especially flavin, to allow the signals from the fluorescent materials to be substantially equal to each other.

Figure 8:
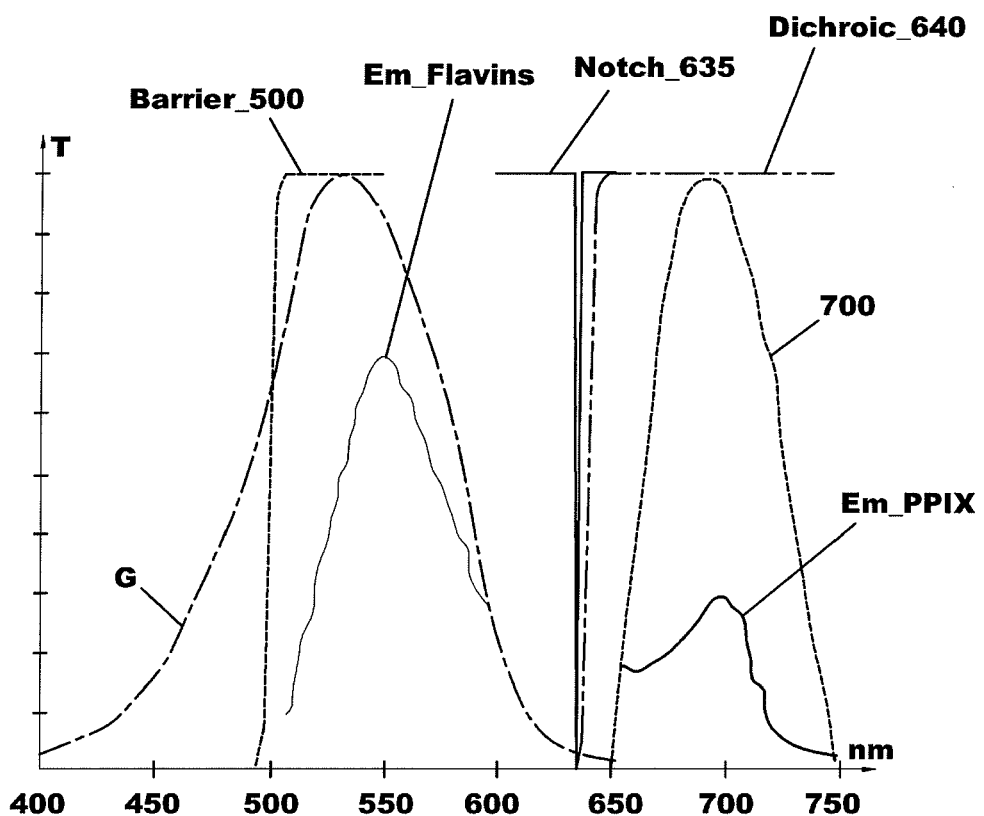
FIG. 8 shows fluorescence emission spectral curves of flavin and PpIX and transmission spectral curves of G and far-red/near-infrared (FR/NIR) channels in the multispectral imaging system in accordance with the present invention.

The solution of problem (a) has been described in Example 1-3. A mercury lamp having a wavelength of 455 nm was used in the filter EX1 for the excitation of flavins, and a laser light source having a wavelength of 635 nm was used in the laser Ex2 for the excitation of porphyrins (refer to FIG. 5). The solution of problem (d) is possible when the excitation light output of the mercury lamp of Ex1 is controlled by the first attenuator 61. Problems (b) and (c) can be solved by detecting and recording fluorescence of the fluorescent materials by means of the multispectral imaging system. The spectral conditions for the fluorescence recording are shown in FIG. 8.

When the emission reflected from the body tissue is blocked, the filters Ex1 and Ex2 operate together with a barrier filter (500 nm) and a notch filter (635 nm), and the two filters perform the functions of the movable detection filter 42. In this case, the edge value of the dichroic mirror 43 should be slightly beyond 635 nm (640 nm in this example). PpIX fluorescence is separated from flavin fluorescence by the dichroic mirror. In the PpIX emission fluorescence, an additional wavelength (700 nm center) is selected by the detection filter (Em2) 46 disposed in the far-red/near-infrared (FR/NIR) channel. This band-pass filter transmits the fluorescence generated from PpIX to the monochrome image sensor 47 and attenuates the excitation laser beam together with the notch filter (635 nm) (an additional band-pass filter was used in the fluorescence channel to reject the residual excitation light).

An image produced by the flavins in the spectral channel of the G color image sensor has a signal to noise ratio greater than that of the monochrome image sensor. Since the flavin is present in all cells, a "green image" produced by the flavin is seen as more uniform than a "red image" produced by the PpIX. Thus, the "green image" may serves as a reference function that can be used to correct the PpIX fluorescent signal value for the effect of the distance to the object tissue and provide anatomic identification in the position of PpIX.

As such, the optimization of the excitation conditions and the fluorescence recording is made, and thus a small amount of endogenous porphyrins can be easily observed in the channel of the monochrome image sensor rather than the G color image sensor. On the contrary, in the conventional apparatuses, the stronger intrinsic fluorescence occurring all over the body tissue interferes with the detection of weak fluorescent signal s of PpIX. Since the weak fluorescence of PpIX generated endogenously can be displayed as an image, it is possible to perform non-ALA fluorescence diagnosis without the administration of ALA from the outside and thus perform screening test for disease diagnosis.

5. Photodynamic Therapy and Fluorescence Detection

This process was related to photodynamic therapy (PDT), in which a photosensitizer (PS) emitting a predetermined wavelength was administered to the body tissue and then the body tissue was illuminated. Since the fluorescence emission is generated from the photosensitizer by the illumination, the fluorescence detection can be used for optimization and monitoring of the photodynamic therapy. The fluorescence detection can be used to trace is kinetic accumulation of the photosensitizer, identify a local area where the photosensitizer was accumulated, and evaluate the effects of the photodynamic therapy.

According to the present invention, it is possible to change the illumination area and determine the time point at which the illumination is finished by directly detecting the fluorescence during the photodynamic therapy. In this case, the function (dosimetry) of determining the time point at which the illumination is finished uses photobleaching of the photosensitizer. Since the fluorescence of the photosensitizer has local characteristics, it is necessary to provide a reference image, which can cover the entire object tissue, for the fluorescence observation. And the reference image can be used to correct data according to a change in distance to the object tissue during measurement.

The illumination on the surface of the body tissue and the production of images therefrom may be performed by various methods. One of them has been described in Example 2-2, which corresponds to the conditions where main and reference fluorescence images are produced by each other light source and each other detector. The second method will be described in Example 3-1, in which images are produced by one light source and one detector. And, the third method, which will be described in Example 4-1, uses a reflectance image as the reference image, differently from the first and second methods. The above-described methods allow an operator to view the object tissue during illumination and to measure the fluorescence brightness caused by the photosensitizer in real time. A histogram that shows the distribution of the brightness in a shot was calculated so that the measured fluorescence brightness would not depend on the area occupied by the photosensitizer in the shot, and the brightest region was measured based on the same.

The illumination process was maintained under predetermined conditions, and the illumination area was corrected, if necessary. Moreover, when the photobleaching reached a predetermined degree, the illumination was stopped, thus increasing the effects of the photodynamic therapy.

Example 3-1

Fluorescence Diagnosis and Photodynamic Therapy with ALA-Induced PpIX

Figure 9:
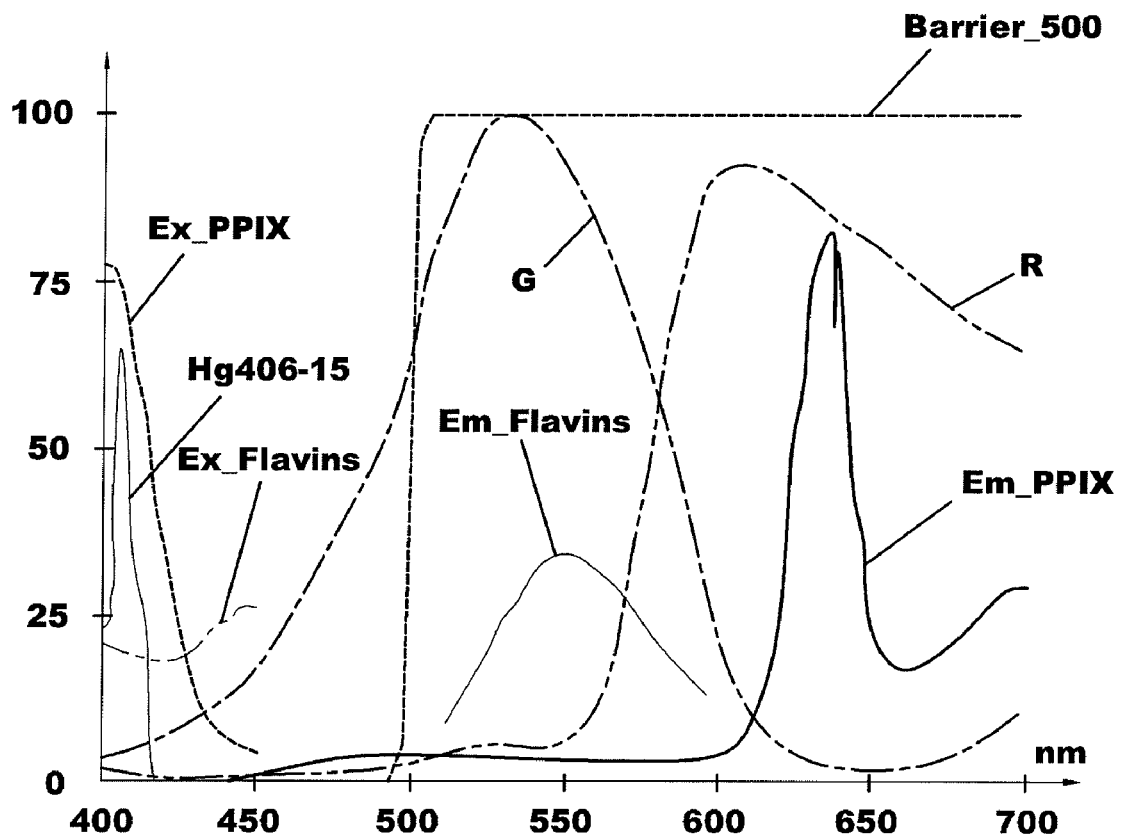
FIG. 9 shows spectral curves for flavin and ALA-induced PpIX fluorescence detection by blue light and photodynamic therapy in the multispectral imaging system in accordance with the present invention.

Since the aminolevulinic acid (ALA) is changed into protoporphyrin (PpIX) in the body tissue, the illumination and fluorescence detection optics are substantially the same as Example 2-2. In this example, the illumination with a short-wavelength around the porphyrin's Soret band (about 400 nm) will be described. In this case, the illumination may be performed with a mercury lamp, and the illumination with a short-wavelength is used when the surface of the body tissue is damaged. When the ALA is used, the concentration of PpIX in the body tissue considerably exceeds the concentration of PpIX generated endogenously, which enables the fluorescence recording in the color image sensor having a sensitivity lower than that of the monochrome image sensor. The optical spectra of the illumination and the conditions for the fluorescence recording are shown in FIG. 9.

The light source Ex1 (406 nm) performs several functions such as performing photodynamic therapy, generating intrinsic fluorescence emission, and exciting fluorescence by illuminating the ALA-induced PpIX simultaneously. The intrinsic fluorescence is recorded in the G channel of the color image sensor, and the ALA-induced PpIX fluorescence is recorded in the R channel of the color image sensor. The brightness of the fluorescence in the R channel is changed during illumination and, when the fluorescence brightness is reduced from the initial value to a predetermined value, the illumination is stopped. When the existence of a disease can be determined by an increase in red fluorescence by the ALA-induced PpIX, it is possible to use similar illumination and recording conditions in the ALA fluorescence diagnosis.

6. Fluorescence/Reflectance Detection

This process is performed to obtain a reflectance image and a fluorescence image simultaneously. The reflectance image can be used together with the fluorescence image for the purpose of diagnosis and serve as the reference image. The spectral region of the fluorescence excitation and that of the reflectance light may be identical to or different from each other. The possibility of the use of an apparatus for simultaneous observation in the fluorescence and reflectance light may be shown in an example of fluorescence angiography in the near-infrared spectral range.

Example 4-1

Fluorescence Angiography Using Indocyanine Green (ICG)

The fluorescence angiography is a well-known method for detecting blood vessels in a patient's eye in ophthalmology and widely applied in various fields such as orthopedics. As a fluorescent contrast agent, fluorescein and ICG are used, which enter the blood circulation system to trace the blood flow. The characteristics of the ICG are that it emits fluorescence in the near-infrared region and the examination can be performed in a bright room.

Meanwhile, Novadaq Technologies Inc. (http/www.novadaq.com) manufactures SPY imaging system for the purpose of fluorescence angiography using ICG contrast agent. This system can provide only an ICG fluorescence video image. In this case, the video observation recording and the fluorescence recording cannot be made simultaneously in the reflectance white light, and thus it is difficult to combine two images into one image.

Figure 10:
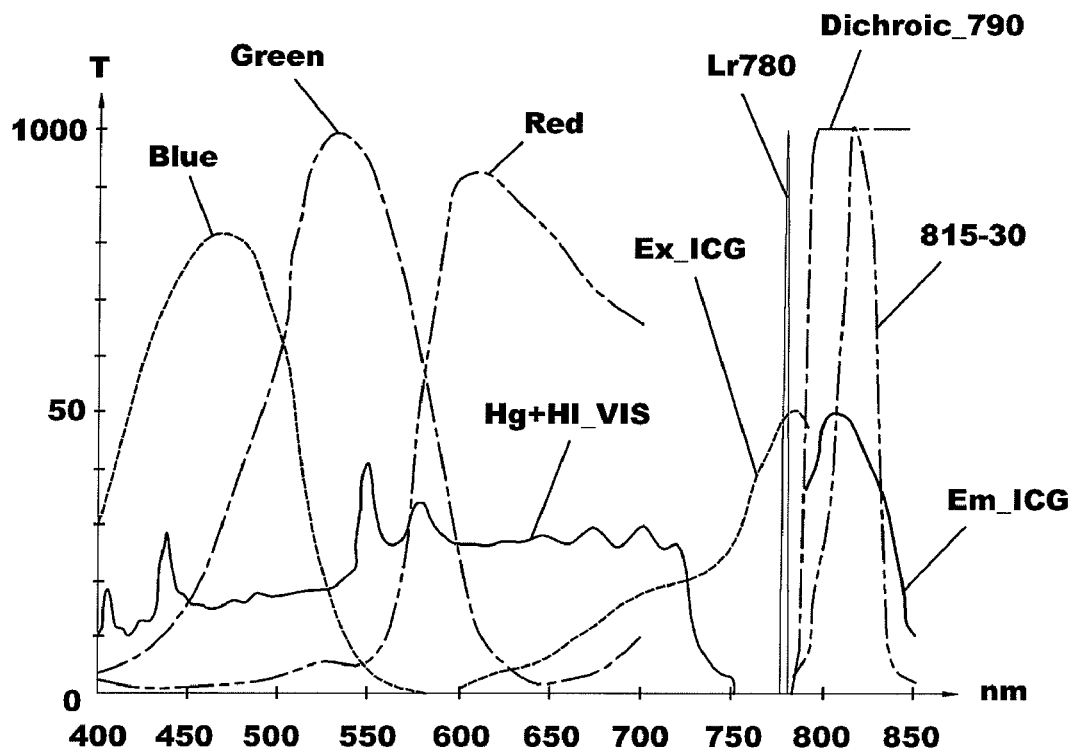
FIG. 10 shows spectral curves for fluorescence angiography by indocyanine green (ICG) in the multispectral imaging system in accordance with the present invention.

The apparatus for photodynamic therapy and photodetection in accordance with the present invention can perform the operation of obtaining a combined image. The illumination and the spectral conditions for this operation are shown in FIG. 10. In this case, the object tissue is illuminated with several emission light sources simultaneously. Mercury and halogen lamps (Ex1: 400 to 750 nm) as a white light source serves to obtain a general image in the reflectance light, and a laser (Ex2: 780 nm) is prepared for the fluorescence excitation of ICG. Moreover, in the near-infrared excitation emission having a long-wavelength of more than 790 nm, operating room surgical lamps may serve as the white light source. The color image sensor for detecting the reflectance white light produces a high grade color image by the R, G, and B channels, and the indocyanine green ICG fluorescence produces a monochrome image by the near-infrared channel (Em2: 815 nm) of the monochrome image sensor. In this example, the detection filter (Em1) is not used. The emission lights of the filter Ex1 and the filter Ex2 reflected from the body tissue are blocked by the dichroic mirror having an edge of 790 nm in the near-infrared channel and the detection filter (Em2: 815±15 nm). Under these conditions, a reflectance white light image and a fluorescence image of blood vessels by the ICG are simultaneously produced. These images overlap each other and are displayed on a monitor screen in a single color image. The image produced by the white light serves as a reference image. The positions of blood vessels for morphological components of the body tissue are determined by the image, and automatic focusing is performed. The given conditions can be applied to any photodynamic therapy using NIR photosensitizers as well as the fluorescence angiography.

As described above, the apparatus for photodynamic therapy and photodetection in accordance with the present invention has the following effects.

First, with the use of the apparatus for photodynamic therapy and photodetection of the present invention, it is possible to perform photodiagnosis by producing a multispectral image of tissue and photodynamic therapy by illuminating the tissue.

Second, the apparatus for photodynamic therapy and photodetection of the present invention can perform the following operations:

(1) The multispectral imaging system is located between the objective lens and the variable power optical systems to use the emission light passing through the aperture of the objective lens such that a larger amount of light can be introduced into the detector, and thus it is possible to effectively record a weak fluorescence image;

(2) With the use of the folding mirror, it is possible to include or exclude the imaging system in or from the optical path so as to three-dimensionally observe the object tissue, and thus it is possible to easily control the medical tool against the body tissue;

(3) In the illumination light source that mixes lights emitted from the mercury lamp and the halogen lamp the attenuator is located in front of the mercury lamp, and thus the color of the illumination light source can be flexibly changed by controlling the attenuator according to a selected operation (visual observation in white light, TV observation, and oxygenation measurement);

(4) Since the lights of the two light sources such as the mercury lamp and the laser are mixed with each other, it is possible to perform the illumination for fluorescence excitation onto the object tissue with different two wavelengths in the ultraviolet, visible, and near-infrared spectral ranges at the same time, and thus it is possible to provide optimal excitation of two different fluorescent materials and perform observation and photodynamic therapy on the object tissue at the same time from the two fluorescent materials (photosensitizer) and the endogenous materials of the body tissue;

(5) The lights emitted from the laser and the lamp light sources are introduced into the same light guide, and thus it provides uniform illumination to the field of view at different wavelengths under the same illumination conditions;

(6) The illumination filter wheel is disposed only on the optical path of the mercury lamp, and thus it is possible to transmit the emission of lights from other broadband and monochromatic light sources to the light guide at the same time without attenuation of light;

(7) Since the multispectral imaging system includes the color image sensor and the monochrome image sensor, it is possible to simultaneously obtain images in four spectral channels disposed in the visible and near-infrared spectral ranges and simultaneously observe the object tissue in white light and fluorescence. And, the thus obtained image has a high resolution compared to the case where each section in a single sensor is used to simultaneously obtain images in different spectral ranges;

(8) With the use of the movable optical path split means capable of escaping from the optical path of the color image sensor, there is no light loss under the conditions where only the color image sensor operates; and (9) The movable detection filter located in front of the movable optical path split means affects the spectral components of the lights transmitted to both sensors, and thus it is possible to remotely change the detection conditions without replacing the filters in front of the sensors with hands.

Third, the apparatus for photodynamic therapy and photodetection of the present invention is configured to perform simultaneous operations on various spectral components, and thus it has the following effects:

(1) It is possible to use a broadband illumination source to observe and record an image of the body tissue (for example, the spectral components of the illumination in white light can be changed by changing the color temperature of the emission light), and thus it is possible to select optimal spectral components in accordance with the characteristics of the detector, the properties of the body tissue, and the purpose of research;

(2) It is possible to observe and record an image of the body tissue in reflectance light and simultaneously observe fluorescence and reflectance light in the visible and near-infrared regions;

(3) It is possible to excite fluorescence by emission of various wavelengths and simultaneously detect fluorescence in several spectral channels, and thus it is possible to provide optimal excitation conditions to each of several fluorescent materials and observe and measure the fluorescence in real time;

(4) Since it is possible to simultaneously perform the photodynamic therapy and fluorescence diagnosis, it is possible to trace kinetic accumulation of the photosensitizer, identify a local area where the photosensitizer is accumulated, evaluate the effects of the photodynamic therapy, and directly observe the fluorescence image during the photodynamic therapy. As a result, it is possible to correct the illuminated area and determine the time point at which the illumination is finished using the photobleaching effect of the photosensitizer; and (5) Since the detection of fluorescence and reflectance can be performed simultaneously, it is possible to produce a synthesized image in real time, and thus it is possible to simultaneously provide a fluorescence image for providing information related to biochemical or physiological characteristics of a body part and an image in the reflectance light that shows its morphological aspects.

As above, preferred embodiments of the present invention have been described and illustrated, however, the present invention is not limited thereto, rather, it should be understood that various modifications and variations of the present invention can be made thereto by those skilled in the art without departing from the spirit and the technical scope of the present invention as defined by the appended claims.

What is claimed is:

1. An apparatus for photodynamic therapy and photodetection, which provides illumination with light of various wavelengths and multispectral images, the apparatus comprising:

an optical imaging system producing an image of an object tissue and transmitting the image to a naked eye or an imaging device;
a combined light source including a plurality of coherent and non-coherent light sources and a light guide guiding incident light emitted from the light sources;
a multispectral imaging system including at least one sensor; and a computer system outputting an image of the object tissue to the outside, wherein the multispectral imaging system comprises two image sensors wherein the two image sensors comprise a color image sensor and a monochrome image sensor, and wherein the multispectral imaging system further comprises an optical path split means for splitting incident light to have two optical paths for the color image sensor and the monochrome image sensor.

2. The apparatus of claim 1, wherein the combined light source comprises a first light source, a second light source, and a third light source.

3. The apparatus of claim 2, wherein the first light source is a mercury lamp.

4. The apparatus of claim 3, further comprising a first filter for controlling the light emitted from the mercury lamp as the first light source and introduced into the light guide.

5. The apparatus of claim 4, wherein the first filter is located between the mercury lamp and the light guide and disposed on an optical path for the mercury lamp so as not to interfere with optical paths from the light sources other than the mercury lamp.

6. The apparatus of claim 5, wherein the first filter is provided in the form of a filter wheel to include a plurality of optical elements in divided areas on the rotational surface of the filter wheel.

7. The apparatus of claim 6, wherein the plurality of optical elements comprise at least two selected from the group consisting of a short-pass filter, a band-pass filter, and a polarizer.

8. The apparatus of claim 4, further comprising a first attenuator located on the optical path of the first light source to control the amount of light from the mercury lamp.

9. The apparatus of claim 8, further comprising a second attenuator disposed at an inlet of the light guide to control the total amount of light introduced into the light guide.

10. The apparatus of claim 3, wherein the mercury lamp is a mercury lamp having a band-pass filter (327 to 353 nm).

11. The apparatus of claim 3, wherein the mercury lamp is a mercury lamp having a band-pass filter (440 to 470 nm).

12. The apparatus of claim 2, wherein the second light source is a halogen lamp.

13. The apparatus of claim 12, further comprising a first mirror configured to change the path of light emitted from the halogen lamp as the second light source to be introduced into the light guide.

14. The apparatus of claim 13, wherein the first mirror is a dichroic mirror for selectively transmitting light based on a wavelength.

15. The apparatus of claim 13, further comprising a second filter disposed between the halogen lamp and the first mirror to block infrared radiation.

16. The apparatus of claim 13, wherein the third light source comprises a plurality of lasers, and the plurality of second mirrors are located on the paths of a plurality of laser beams generated from the plurality of lasers such that the plurality of laser beams are introduced into the light guide through the second mirrors.

17. The apparatus of claim 16, wherein the second mirror is a dichroic mirror.

18. The apparatus of claim 2, wherein the third light source is a laser.

19. The apparatus of claim 18, wherein a laser beam generated from the laser as the third light source is directly introduced into the light guide.

20. The apparatus of claim 18, wherein the laser (405 nm) as excitation light sources for simultaneously exciting NADH and flavin.

21. The apparatus of claim 18, wherein the laser (635 nm) as excitation light sources for simultaneously exciting flavin and porphyrin.

22. The apparatus of claim 1, further comprising a collimating optics disposed at an outlet of the light guide to provide uniform illumination to the field of view.

23. The apparatus of claim 22, further comprising an attached light guide module provided in the collimating optics to provide illumination to a smaller area.

24. The apparatus of claim 1, wherein the light guide is a liquid light guide.

25. The apparatus of claim 1, wherein the optical imaging system is one selected from the group consisting of an endoscope, an operating stereo microscope, and a colposcope.

26. The apparatus of claim 25, wherein when the optical imaging system is the endoscope, the multispectral imaging system is fixed to an eyepiece of the optical imaging system by means of an adaptor.

27. The apparatus of claim 25, wherein when the optical imaging system is the operating stereo microscope, the optical imaging system comprises an objective lens and a pair of variable power optical systems, and the multispectral imaging system is located between the objective lens and the variable power optical systems.

28. The apparatus of claim 27, wherein the multispectral imaging system enters the optical path through a movable folding mirror disposed between the objective lens and the variable power optical systems of the optical imaging system.

29. The apparatus of claim 1, wherein the objective lens of the multispectral imaging system is located in front of the optical path split means to project an image to the two optical paths of the color image sensor and the monochrome image sensor simultaneously.

30. The apparatus of claim 29, wherein the objective lens comprises an aperture stop to control the amount of light and the depth of field.

31. The apparatus of claim 29, wherein the objective lens comprises a focusing element for fine focus adjustment on the object tissue.

32. The apparatus of claim 29, wherein fluorescence detection of NADH and flavin is simultaneously performed by B and G channels of the color image sensor.

33. The apparatus of claim 29, wherein a movable detection filter in the form of a filter wheel is located in front or rear of the objective lens of the multispectral imaging system, and the movable detection filter comprises at least two selected from the group consisting of a long-pass filter, a band-pass filter, a notch filter, an analyzer, and a polarizer.

34. The apparatus of claim 33, wherein the movable detection filter comprises a blocking filter (500 nm) and a notch filter (635 nm) such that fluorescence of porphyrin is detected by the monochrome image sensor through the far-red/near-infrared filter by the dichroic mirror (edge 640 nm) and, at the same time, fluorescence of flavin is detected by the color image sensor (G channel).

35. The apparatus of claim 29, wherein an infrared blocking filter is located in front of the color image sensor of the multispectral imaging system, and a far-red/near-infrared filter is located in front of the monochrome image sensor.

36. The apparatus of claim 1, wherein the optical path split means is a movable folding mirror.

37. The apparatus of claim 36, wherein the movable folding mirror is a dichroic mirror.

38. The apparatus of claim 1, further comprising an image processing controlling unit for controlling the color image sensor and the monochrome image sensor.

39. The apparatus of claim 38, further comprising a computer system for outputting an image from the multispectral imaging system to the outside.

40. An apparatus for photodynamic therapy and photodetection, which provides illumination with light of various wavelengths and multispectral images, the apparatus comprising:
- an optical imaging system producing an image of an object tissue and transmitting the image to a naked eye or an imaging device;
- a combined light source including a plurality of coherent and non-coherent light sources and a light guide guiding incident light emitted from the light sources;
- a multispectral imaging system including at least one sensor;
- a computer system outputting an image of the object tissue to the outside;
- a collimating optics disposed at an outlet of the light guide to provide uniform illumination to the field of view; and
- an attached light guide module provided in the collimating optics to provide illumination to a smaller area.

* * * * *